(12) United States Patent
Tegg et al.

(10) Patent No.: US 11,420,019 B2
(45) Date of Patent: Aug. 23, 2022

(54) UNIBODY INTRAVASCULAR CATHETER SHAFT

(71) Applicant: St. Jude Medical, Cardiology Division, Inc., St. Paul, MN (US)

(72) Inventors: Troy T. Tegg, Elk River, MN (US); Gregory K. Olson, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 366 days.

(21) Appl. No.: 16/564,082

(22) Filed: Sep. 9, 2019

(65) Prior Publication Data

US 2020/0078560 A1    Mar. 12, 2020

Related U.S. Application Data

(60) Provisional application No. 62/729,976, filed on Sep. 11, 2018.

(51) Int. Cl.
| | | |
|---|---|---|
| *A61M 25/01* | (2006.01) | |
| *A61M 25/00* | (2006.01) | |
| *A61B 5/00* | (2006.01) | |

(52) U.S. Cl.
CPC .... *A61M 25/0147* (2013.01); *A61M 25/0045* (2013.01); *A61M 25/0053* (2013.01); *A61B 5/0035* (2013.01); *A61B 5/6852* (2013.01); *A61M 25/0012* (2013.01); *A61M 25/0068* (2013.01); *A61M 2025/0183* (2013.01)

(58) Field of Classification Search
CPC .......... A61M 25/0147; A61M 25/0045; A61M 25/0053; A61B 5/0035; A61B 5/6852

USPC ....................................................... 604/527
See application file for complete search history.

(56) References Cited

U.S. PATENT DOCUMENTS

| | | |
|---|---|---|
| 6,233,476 B1 | 5/2001 | Strommer et al. |
| 6,498,944 B1 | 12/2002 | Ben-Haim et al. |
| 6,690,963 B2 | 2/2004 | Ben-Haim et al. |
| 7,197,354 B2 | 3/2007 | Sobe |
| 7,263,397 B2 | 8/2007 | Hauck et al. |
| 7,386,339 B2 | 6/2008 | Strommer et al. |

(Continued)

OTHER PUBLICATIONS

Japan Patent Office Notice of Reasons for Rejection issued in patent family application 2020571629, dated Mar. 29, 2022.

*Primary Examiner* — Phillip A Gray
(74) *Attorney, Agent, or Firm* — Kilpatrick Townsend & Stockton LLP

(57) ABSTRACT

Aspects of the present disclosure are directed to a unibody intravascular catheter shaft with benefits which may include a reduced diameter, and independently tunable torquability, flexibility, and pushability characteristics. While various embodiments of the present disclosure may be directed to an entire catheter shaft, various specific embodiments of the present disclosure may be directed to a unibody shaft design, which may be implemented in a portion of a catheter shaft. For example, the unibody shaft design may be advantageously implemented in a proximal shaft portion. Moreover, various embodiments of the present disclosure utilize a modular unibody design, which may be utilized for various catheter shaft applications using an outer polymer layer with variable thickness and durometer to achieve application-specific performance characteristics (e.g., catheter shaft flex).

20 Claims, 5 Drawing Sheets

(56) References Cited

U.S. PATENT DOCUMENTS

| | | |
|---|---|---|
| 7,465,288 B2 | 12/2008 | Dudney et al. |
| 7,536,218 B2 | 5/2009 | Govari et al. |
| 9,358,066 B2 | 6/2016 | Brannan |
| 2004/0122360 A1 | 6/2004 | Waldhauser et al. |
| 2012/0259326 A1* | 10/2012 | Brannan ............ A61B 18/1492 606/33 |
| 2014/0200441 A1* | 7/2014 | Potter ................ A61M 3/0279 600/549 |
| 2017/0354463 A1 | 12/2017 | Mori |
| 2018/0125367 A1 | 5/2018 | Gliner et al. |
| 2018/0177467 A1 | 6/2018 | Katz et al. |

* cited by examiner

UNIBODY INTRAVASCULAR CATHETER SHAFT

CROSS-REFERENCE TO RELATED APPLICATION

This application claims the benefit of U.S. provisional application No. 62/729,976, filed 11 Sep. 2018, which is hereby incorporated by reference as though fully set forth herein.

BACKGROUND OF THE INVENTION a. Field of the Invention

The instant disclosure relates generally to a unibody catheter shaft, and an intravascular catheter incorporating a unibody catheter shaft section.

b. Background Art

Intravascular catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions and stasis of blood flow in a chamber of a heart which can lead to a variety of symptomatic and asymptomatic ailments and even death.

Typically, an intravascular catheter is deployed and manipulated through a patient's vasculature to the intended site, for example, a site within a patient's heart or a chamber or vein thereof. The catheter carries one or more electrodes that can be used for cardiac mapping or diagnosis, ablation and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. The catheter imparts ablative energy to cardiac tissue to create one or more lesions in the cardiac tissue and oftentimes a contiguous or linear and transmural lesion. This lesion disrupts undesirable cardiac activation pathways and thereby limits, corrals, or prevents errant conduction signals that can form the basis for arrhythmias.

To position a catheter at a desired site within the body, some type of navigation may be used, such as mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to position the distal portion of the catheter during an electrophysiological procedure. The proximal end of the catheter can be manipulated to guide the catheter through a patient's vasculature. The distal tip can be deflected by a pull wire attached at the distal end of the catheter that extends to a control handle that controls the application of tension on the pull wire.

Two of the mechanical considerations for a catheter shaft are that it transmit torque and resist compression during use. With respect to transmitting torque, medical personnel normally navigate the distal end of the catheter to a desired location in part by manipulating a handle disposed at the proximal end of the catheter. Substantial frictional forces sometimes resist transmission of torque across the length of the catheter. In some cases, these forces can cause the catheter shaft to twist about a longitudinal axis of the catheter shaft, storing energy in the process (in a spring-like fashion). If the energy is released suddenly, the distal end of the catheter, which may be deflected by a steering mechanism, can be undesirably propelled with significant force.

With respect to resisting compression during use, it is important for medical personnel to be able to advance the catheter through a vessel, sometimes against significant frictional resistance, without undue axial compression or snaking of the catheter shaft. Shaft compression can result in a loss of control for the medical practitioner and can complicate the positioning of the distal end of the catheter shaft at a desired location for a medical procedure. In addition, medical personnel may rely on tactile feedback to attain and verify proper positioning of the catheter, and such feedback may be impaired by excessive compressibility.

The foregoing discussion is intended only to illustrate the present field and should not be taken as a disavowal of claim scope.

BRIEF SUMMARY OF THE INVENTION

Various aspects of the present disclosure are directed to a unibody catheter shaft section and intravascular catheter systems utilizing such unibody catheter shaft sections to achieve desirable force transmission characteristics.

Unibody intravascular catheter shafts consistent with the present disclosure have benefits including a reduced diameter, and independently tunable torquability, flexibility, and pushability characteristics. While various embodiments of the present disclosure may be directed to an entire catheter shaft, various specific embodiments of the present disclosure may be directed to a unibody shaft design, which may be implemented in a portion of a catheter shaft. For example, the unibody shaft design may be advantageously implemented in a proximal shaft portion. Moreover, various embodiments of the present disclosure utilize a modular unibody design, which may be utilized for various catheter shaft applications using an outer polymer layer with variable thickness and durometer to achieve application-specific performance characteristics (e.g., catheter shaft flex).

Aspects of the present disclosure may be readily applied to a variety of intravascular catheters (e.g., electrophysiology catheters, ablation catheters, imaging catheters, steerable sheaths). Some specific implementations of the unibody intravascular catheter shaft may be compatible with magnetic resonance imaging ("MRI") systems.

Various aspects of the present disclosure are directed to a proximal catheter shaft design that utilizes center out construction techniques, as opposed to prior implementations that build the catheter shaft outside in.

One embodiment of the present disclosure is directed to a deflectable catheter shaft including a unibody core, a braid, and a reflowed polymeric material. Wherein the unibody core includes a plurality of lumens extending along a longitudinal axis of the catheter shaft, the braid circumferentially and longitudinally encompasses the plurality of lumens, and the reflowed polymeric material fills gaps between the plurality of lumens and the braid. The catheter shaft has independently tunable mechanical characteristics. In further more specific embodiments, the plurality of lumens include a central fluid lumen, and a plurality of electrical and pull-wire lumens extending around the central fluid lumen.

In another embodiment of the present disclosure, an intravascular catheter is disclosed including proximal and distal catheter shaft sections. The proximal catheter shaft section includes a plurality of lumens extending along a longitudinal axis of the catheter shaft, a proximal portion of a braid circumferentially and longitudinally encompassing the plurality of lumens, and a reflowed polymeric material configured and arranged to fill gaps between the plurality of lumens and the braid. The distal catheter shaft section disposed at the distal end of the proximal catheter shaft section, and including a distal portion of the braid extending into the distal catheter shaft section, and a Balun coil and a capacitor coupled to an outer diameter of the braid, and the Balun coil and the capacitor are electrically coupled to one another. In more specific embodiments, the proximal catheter shaft section has independently tunable mechanical characteristics.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings, in which.

Figure 1A:
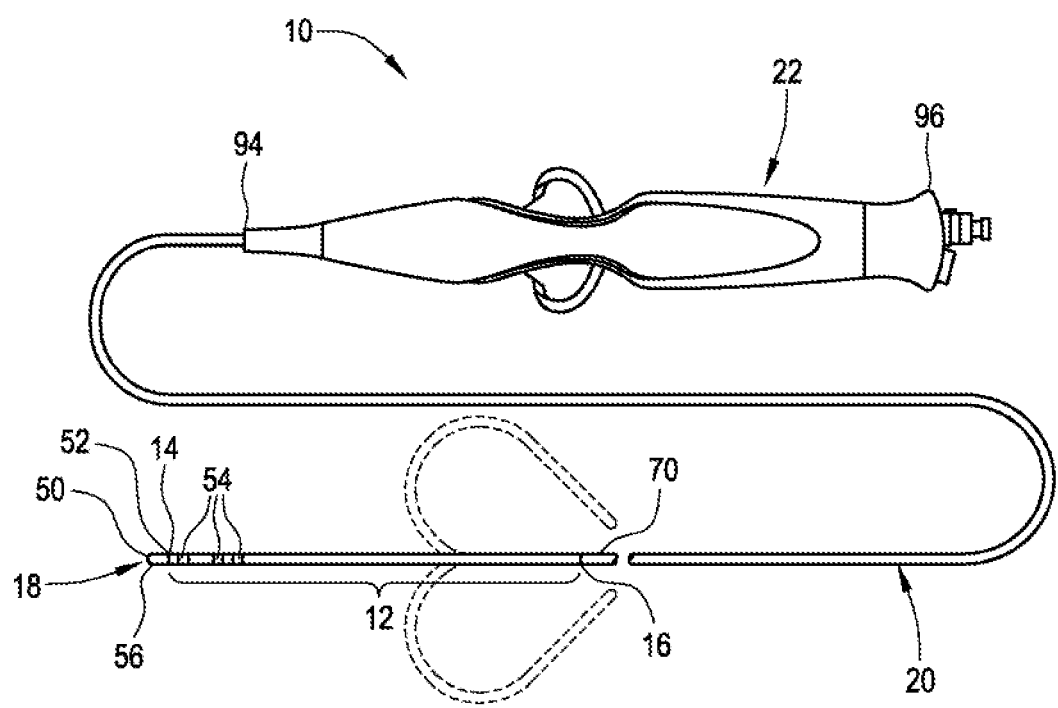
FIG. 1A is a schematic view of a catheter incorporating a unibody catheter shaft section, in accordance with various embodiments of the present disclosure.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF THE DISCLOSURE

Aspects of the present disclosure are directed to a unibody intravascular catheter shaft with benefits including independently tunable torquability, flexibility, and pushability (compression) characteristics. The unibody shaft may also facilitate diameter reduction in various applications. While various embodiments of the present disclosure may be directed to an entire catheter shaft, various specific embodiments of the present disclosure may be directed to a unibody shaft design, which may be implemented in a portion of a catheter shaft. For example, the unibody shaft design may be advantageously implemented in a proximal shaft portion. Moreover, various embodiments of the present disclosure utilize a modular unibody design, which may be utilized for various catheter shaft applications, utilizing an outer polymer layer with variable thickness and durometer to achieve application-specific performance characteristics (e.g., catheter shaft flex).

Aspects of the present disclosure may be readily applied to a variety of intravascular catheters (e.g., electrophysiology catheters, ablation catheters, imaging catheters, steerable sheaths, etc.). Some specific implementations of the unibody intravascular catheter shaft may be compatible with MRI systems.

Various aspects of the present disclosure are directed to proximal catheter shaft design utilizing center out construction techniques, as opposed to prior implementations that build radially inward.

Aspects of the present disclosure are directed to a relatively thin-wall, braided, hollow catheter shaft, which delivers desirable characteristics, including a reduced outer diameter compared to existing catheter shafts and application-configurable torquability, flexibility, and pushability. In one specific embodiment of the present disclosure, a stainless steel flat braid wire is used in conjunction with one or more polymers that melt/flow in between the braid wire during construction/manufacturing. The size of the braid wire, the braid wire's cross-sectional shape (e.g., square or circular), the pitch of the braid wire, the pic size, and the type and durometer of the polymer may be used in combination to change, for example, the torquability of the shaft, as well as the shaft's stiffness and flexibility. However, in such embodiments there may be a trade-off between torque, flexibility, and push characteristics of the shaft.

Various catheter shaft embodiments consistent with the present disclosure effectively decouple the interdependency of shaft torquability, flexibility, and pushability attributes through the separate adjustability or tunability of, for example, the braid material, braid pattern, reflow material (e.g., composition and durability), and outer skin/tubing material (e.g., material type, thickness, and durometer). In prior art catheter shaft designs, these attributes are not independently tunable. Instead, in the prior art catheter shaft designs the single, internal wall primarily controls the torque ability, flexibility/bendability, and push ability of the shaft.

By decoupling the torquability, flexibility, and pushability attributes of the proximal catheter shaft, desirable shaft characteristics may be achieved (e.g., a highly flexible proximal catheter shaft exhibiting a 1:1 or nearly 1:1 torque ratio). With prior catheter shaft construction techniques, one desirable shaft characteristic (e.g., flexibility) may come at the expense of another desirable shaft characteristic (e.g., pushability). Moreover, proximal catheter shaft designs in accordance with the present disclosure benefit from a reduced cross-sectional area to achieve the same characteristics thereby allowing for reduction in diameter (if so desired). In some specific/experimental implementations, a reduction in the proximal catheter shaft outside diameter of 2 French was achieved.

In one specific embodiment of a proximal catheter shaft, consistent with the present disclosure, internal components of the catheter (e.g., fluid/thru lumen(s), and other wire management lumen(s)) provide pushability and flexibility, and a soft braid facilitates torque transmission. The combination of a shaft polymer, soft braid, and the internal components together achieve desirable composite shaft performance.

As discussed above, while aspects of the present disclosure may find broad adoption for intravascular catheter shafts, implementation may be particularly beneficial for applications where catheter shaft diameter reduction is critical; for example, magnetic resonance imaging enabled catheters. In many MRI enabled catheters, a smaller diameter is required, while also fitting additional components required for MRI applications, including for example, braid shield, Balun coils (also referred to as Baluns), and resonance tuning circuitry components.

In various embodiments of the present disclosure, the unibody shaft design may be implemented in a steerable sheath. In such an embodiment, multiple planes of bending may be achieved. In some specific embodiments of the steerable sheath where an increased outer diameter is allowable, lumens for magnetic or voltage tracking sensors and/or other sensors may be accommodated.

While various aspects of the present disclosure are directed to a proximal catheter shaft utilizing a unibody design, a skilled artisan would be capable of integrating the proximal catheter shaft with, for example, a steerable/distal catheter shaft known in the art.

Various unibody, proximal catheter shaft designs, consistent with the present disclosure, decouple pushability and torquability components of the shaft. For example, one or more polyimide lumens within the shaft may be used to control the pushability characteristics of the shaft, and braiding (surrounding the bundle of lumens) may be used to control the torquability characteristics. Moreover, and as discussed above, the unibody catheter shaft design facilitates a more compact design while maintaining the same cross-sectional area for routing lumens.

Aspects of the present disclosure are also directed to a process of manufacturing a unibody catheter shaft consistent with the present disclosure. In one such embodiment, the process includes making a unibody core, encompassing the unibody core within braiding, and adding a polymer outer layer around the shaft with a thickness and durometer which is selected for desirable flexibility for a given application.

Aspects of the present disclosure are also directed to a process of manufacturing a unibody catheter shaft enabled for MRI applications. Such a manufacturing process may include the following steps: forming a unibody core, encompassing the unibody core with braiding, adding one or more Baluns, soldering a capacitor of at least one of the Baluns to the braiding, coupling a coil of at least one of the Baluns to another portion of the braid, and applying a polymer outer layer about the outer circumference of the catheter shaft. In some specific embodiments, the Baluns may be added via an additive building process (directly on to the braiding). In yet other embodiments of the manufacturing process, traces which electrically couple the Baluns and the capacitors may be printed directly to the unibody core.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting or absolute.

FIG. 1A generally illustrates a deflectable intravascular catheter 10 including a deflectable catheter shaft section 12. The deflectable catheter shaft section 12 has a distal end 14 and a proximal end 16. In its most general form, catheter 10 further includes a tip assembly 18 located at the distal end 14 of the deflectable catheter shaft section 12, a proximal catheter shaft section 20 coupled to the proximal end 16 of the deflectable catheter shaft section 12, and a handle assembly 22. Catheter 10 may be used in any number of diagnostic and therapeutic applications, such as the recording of electrograms in the heart, the performance of a cardiac ablation procedure, among other diagnostics and therapeutic procedures. Accordingly, one of ordinary skill in the art will recognize and appreciate that the proximal catheter shaft section 20, including a unibody core, and methods of manufacturing the same may be implemented in any number of diagnostic and therapeutic applications.

Still referring to FIG. 1A, deflectable catheter shaft section 12 is disposed between the tip assembly 18 and the proximal catheter shaft section 20. The length and diameter of the deflectable catheter shaft section 12 can vary according to the application. Generally, the length of the deflectable catheter shaft section 12 can range from about 2 inches (50.8 mm) to about 6 inches (152.4 mm) and the diameter of the deflectable catheter shaft section 12 can range from about 5 French to about 12 French. The diameter of the deflectable catheter shaft section 12 can be about 7 French in accordance with some embodiments of the invention. Although these particular dimensions are mentioned in particular, the dimensions of the deflectable catheter shaft section 12 can vary in accordance with various applications of the deflectable catheter shaft section 12. The deflectable catheter shaft section 12 can be configured for deflection independent of proximal catheter shaft section 20.

The proximal catheter shaft section 20 can be constructed of a series of polymer layer(s) and braid structure(s). In particular, one or more wires wound to form a cylindrical braid structure can substantially surround a plurality of lumens (e.g., fluid lumens, electrical lumens, and pull-wire lumens). In addition, a polymeric material, such as polyurethane, nylon, or various types of plastic materials such as polyether block amides offered under the trademark PEBAX® (which is a registered trademark of Arkema France, Puteaux, France), or any other suitable material, substantially surrounds the braid. A reflow process may be used to fill gaps between each of the lumens and between the lumens and the braid. The material selected for reflow must have the capability to be displaced or to shrink when subjected to a process, such as for example, a heating process that is performed.

The deflectable catheter shaft section 12 can include one or more electrodes (such as, for example, ring electrodes 54) mounted on or affixed to the deflectable catheter shaft section 12. In these particular embodiments, an active outer surface of each electrode 54 can be configured for exposure to blood and/or tissue. Each electrode 54 may be assembled with the deflectable catheter shaft section 12 using any number of known processes. For instance, the electrodes 54 may be built into the deflectable catheter shaft section 12 using a reflow process. In such a process, the electrodes 54 are placed at the appropriate/desired locations on the deflectable catheter shaft section 12, and the deflectable catheter shaft section 12 is exposed to a heating process in which the electrodes 54 and polymeric material forming the deflectable catheter shaft section 12 become affixed or bonded together. Sufficiently sized aperture(s) are formed in the deflectable catheter shaft section 12 proximate to each electrode 54 in order to allow for wires (not shown) connected to the electrodes 54 to be threaded into one of the electrical lumens. The wires may extend through the lumen and may be connected to, for example, monitoring and/or recording devices and/or ablation devices associated with or connected to the catheter 10. These devices are typically located proximate to the handle assembly 22. The wires are typically pre-coated wires such that they are insulated from each other and other components within the catheter 10.

The mechanical properties of the proximal catheter shaft section 20 can be tunable by varying the properties of the cylindrical braid structure(s) and the polymeric material (e.g., dimension of the cylindrical braid structure and/or durometers of the polymers). Additionally, the mechanical properties of the deflectable catheter shaft section 12 can be varied along the length of the deflectable catheter shaft section 12 in accordance with some embodiments of the disclosure or can be substantially constant along the entire length of the deflectable catheter shaft section 12 in accordance with other embodiments of the disclosure.

Referring again to FIG. 1A, proximal catheter shaft section 20 can also include one or more lumens (not shown). Generally, proximal catheter shaft section 20 includes a number of lumens. Proximal catheter shaft section 20 can be constructed of a series of polymer layer(s) and braid structure(s). In particular, one or more wires wound to form a cylindrical braid structure can substantially surround the plurality of lumens of proximal catheter shaft section 20. A unibody structure may be formed by reflowing a polymeric material in the gaps between the lumens and the braid. In addition, a polymeric material, such as polyurethane, nylon, or various types of plastic materials such as polyether block amides offered under the trademark PEBAX®, or any other suitable material, referred to herein as the shaft polymer, can also substantially surround the one or more lumens of proximal catheter shaft section 20. Regardless of the material used, the material must have capability to be displaced or to shrink when subjected to a process, such as for example, a heating process that is performed. The mechanical properties of the proximal catheter shaft section 20 can also be varied by tuning the properties of the cylindrical braid structure(s) and the shaft polymer (e.g., dimension of the cylindrical braid structure and/or thickness/durometer of the shaft polymer). Additionally, the mechanical properties of the proximal catheter shaft section 20 can be varied along a length of the proximal catheter shaft section 20, or can be substantially constant along the entire length of the proximal catheter shaft section 20.

Figure 1B:
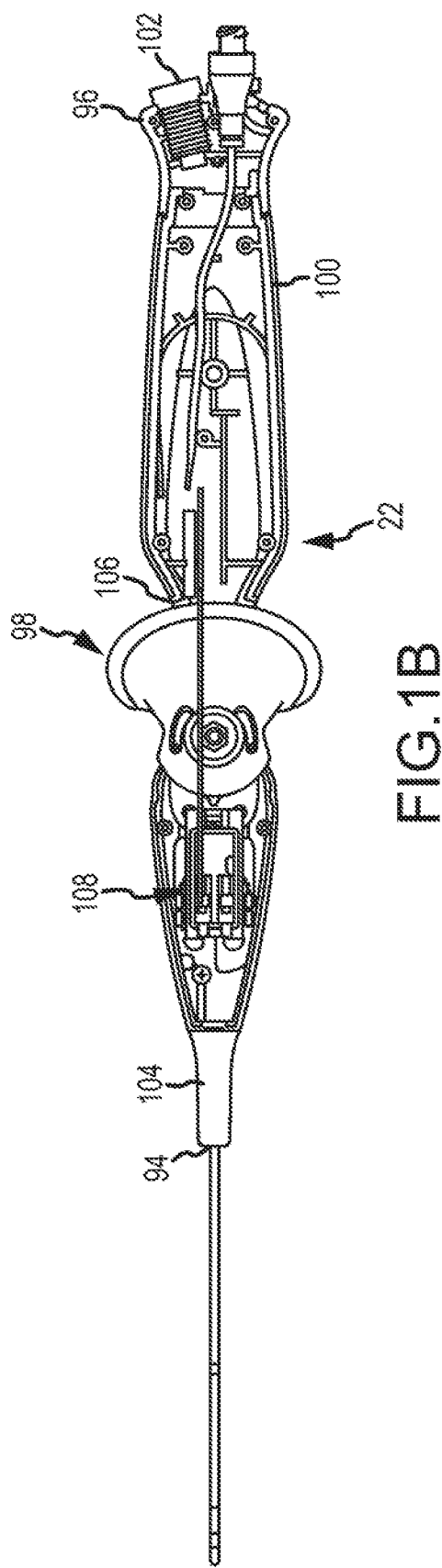
FIG. 1B is a partial cut-away, top view of a handle assembly for the catheter incorporating the unibody catheter shaft section of FIG. 1, in accordance with various embodiments of the present disclosure.
Figure 1C:
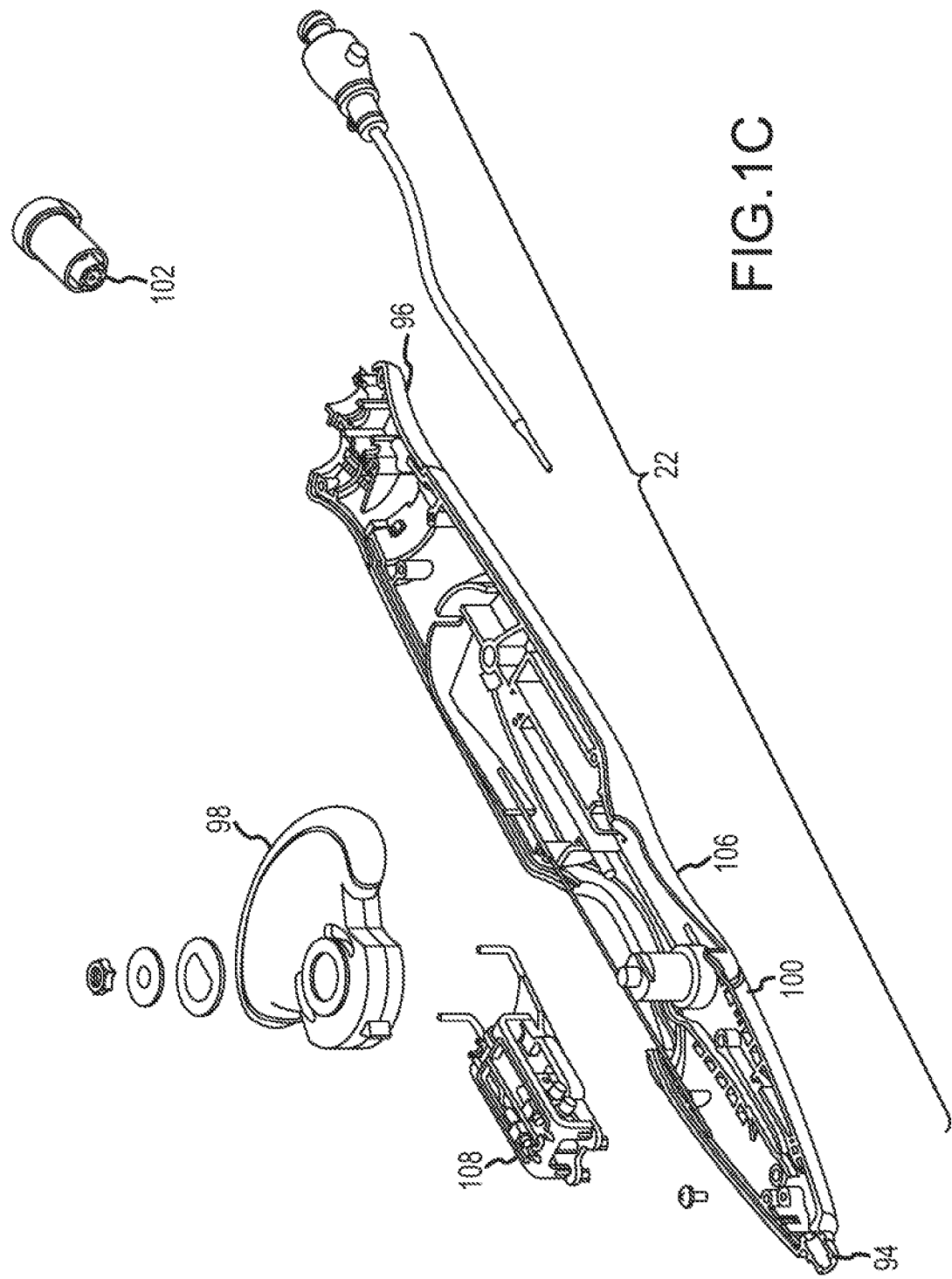
FIG. 1C is a partial, exploded view of the handle assembly of FIG. 1B in accordance with various embodiments of the present disclosure.

With further reference to FIG. 1A, the handle assembly 22 is coupled to the proximal catheter shaft section 20 at its proximal end (disposed within handle assembly 22 and not shown). The handle assembly 22 is operative to, among other things, effect movement (i.e., deflection) of the deflectable catheter shaft section 12. The handle assembly 22 includes a distal end 94 and a proximal end 96. Referring now to FIGS. 1B and 1C, the handle assembly 22 includes an actuator 98 that can be selectively manipulated to cause deflectable catheter shaft section 12 to deflect in one or more directions (e.g., up, down, left, and right). Deflectable catheter shaft section 12 may be configured for uni-directional deflection in accordance with some embodiments of the invention and may be configured for bi-directional deflection in accordance with other embodiments of the invention.

The handle assembly 22 includes an actuator 98, an upper grip portion (not shown), a lower grip portions 100, an electrical plug 102 at the proximal end 96, and a strain relief 104 at the distal end 94. The upper and lower grip portions, when assembled, define a space 106 that extends laterally through the handle assembly 22. The actuator 98 is pivotally coupled to the grip portions 100 and resides in the space 106. The actuator 98 may pivot to bi-directionally deflect the deflectable catheter shaft section 12. Pull wires extend from a pull ring proximally through the deflectable catheter shaft section 12 and the proximal catheter shaft section 20, and into the handle assembly 22. The pull sires coupling to an actuation mechanism 108 of the actuator 98. The upper and lower grip portions are adapted to matingly couple with each other and serve as an enclosure and mounting base for the actuation mechanism 108. The electrical plug 102 is adapted to be connected to a monitoring, recording, and/or an ablation control system. The electrical plug 102 is mounted in a proximal end assembly that serves as the proximal end 96 of the handle assembly 22. The structure and function of the actuation mechanism 108 and the actuator 98 is described in detail in U.S. Pat. No. 7,465,288, which is hereby incorporated by reference as though set forth in its entirety.

The catheter 10 may include any number of other elements such as, for example and without limitation, thermocouples, thermistor temperature sensors, etc. for monitoring the temperature of targeted tissue and may be communicatively coupled to, for example, an ablation control system.

With further reference to FIGS. 1A-C, the catheter 10 may be configured for omni-directional deflection in three-dimensional space. Catheter 10 may be an ablation catheter (i.e., either irrigated or non-irrigated), an electrophysiology catheter (i.e., either electrode or non-electrode based), or other types of catheters well known in the art. Although not shown, catheter 10 may be configured for use with external electronics to facilitate such functionality, and may comprise, in the case of a mapping catheter, visualization, mapping and navigation/localization components known in the art, including among others, for example, an EnSite Velocity™ system running a version of NavX™ software commercially available from St. Jude Medical, Inc., of St. Paul, Minn. and as also seen generally by reference to U.S. Pat. No. 7,263,397 entitled "Method and Apparatus for Catheter Navigation and Location and Mapping in the Heart" to Hauck et al., owned by the common assignee of the present invention, and hereby incorporated by reference in its entirety. Additionally, an electrophysiological (EP) monitor or display such as an electrogram signal display or other systems conventional in the art may also be coupled (directly or indirectly). Such an external localization system may comprise conventional apparatus known generally in the art, for example, an EnSite Velocity™ system described above or other known technologies for locating/navigating a catheter in space (and for visualization), including for example, the CARTO™ visualization and location system of Biosense Webster, Inc., (e.g., as exemplified by U.S. Pat. No. 6,690,963 entitled "System for Determining the Location and Orientation of an Invasive Medical Instrument" hereby incorporated by reference in its entirety), the AURORA® system of Northern Digital Inc., a magnetic field based localization system such as the gMPS™ system based on technology from MediGuide Ltd. of Haifa, Israel and now owned by St. Jude Medical, Inc. (e.g., as exemplified by U.S. Pat. Nos. 7,386,339, 7,197,354 and 6,233,476, all of which are hereby incorporated by reference in their entireties) or a hybrid magnetic field-impedance based system, such as the CARTO 3™ visualization and location system of Biosense Webster, Inc. (e.g., as exemplified by U.S. Pat. No. 7,536,218, hereby incorporated by reference in its entirety). Some of the localization, navigation and/or visualization systems may involve providing a sensor for producing signals indicative of catheter location information, and may include, for example one or more electrodes in the case of an impedance-based localization system such as the EnSite™ Velocity system running NavX™ software.

In the case of an electrophysiology catheter system including tissue ablation functionality, it should be understood that such a system may, and typically will, include other structures and functions omitted herein for clarity, such as one or more body surface electrodes (skin patches) for application onto the body of a patient (e.g., an RF dispersive indifferent electrode/patch for RF ablation), and at least one irrigation fluid source (gravity feed or pump), an RF ablation generator (e.g., such as a commercially available unit sold under the model number IBI-1500T RF Cardiac Ablation Generator, available from Irvine Biomedical, Inc), and the like.

Embodiments of catheters, including those with catheter shafts, as generally illustrated and discussed above, may be readily incorporated with or integrated into catheter 10 for performing ablative procedures. Other types of energy sources (i.e., other than radio-frequency—RF energy) may also be used in connection with catheter 10, such as ultrasound (e.g. high-intensity focused ultrasound), laser, cryogenic, chemical, photo-chemical or other energy used (or combinations and/or hybrids thereof) for performing ablative procedures. Further configurations, such as balloon-based delivery configurations, may be incorporated into catheter 10 in some specific embodiments. Furthermore, various sensing structures may also be included in catheter 10, such as temperature sensors, force sensors, various localization sensors, imaging sensors and the like.

Figure 2:
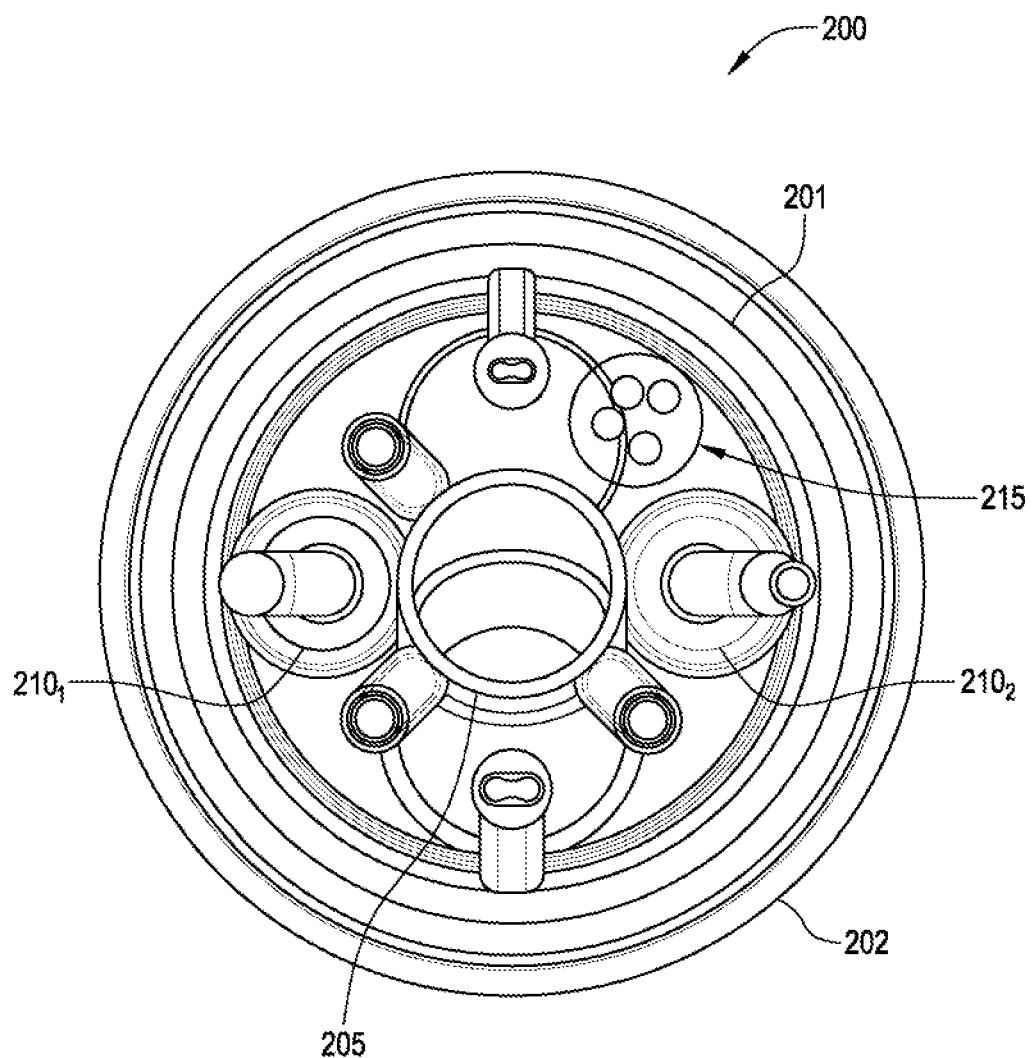
FIG. 2 is a cross-sectional view of a PRIOR ART catheter shaft.

FIG. 2 is a cross-sectional view of a PRIOR ART ablation catheter shaft 200. The catheter shaft 200 includes a central fluid lumen 205 surrounded by pull wire lumens $210_{1-2}$ and electrical lumen 215, among other catheter shaft components. The lumens are circumferentially encompassed by a combination shaft polymer/braid 201 and an outer polyimide tubing 202. The gap between the braid is filled with a shaft polymer to form the shaft polymer/braid 201. Of note, the PRIOR ART ablation catheter shaft 200 may be susceptible to large air gaps or voids between the various components enclosed within the polyimide tubing 202. Moreover, such a catheter shaft design suffers from mechanical characteristic interdependency. That is, a change in the shaft's pushability may negatively impact torque transmission, for example.

Figure 3A:
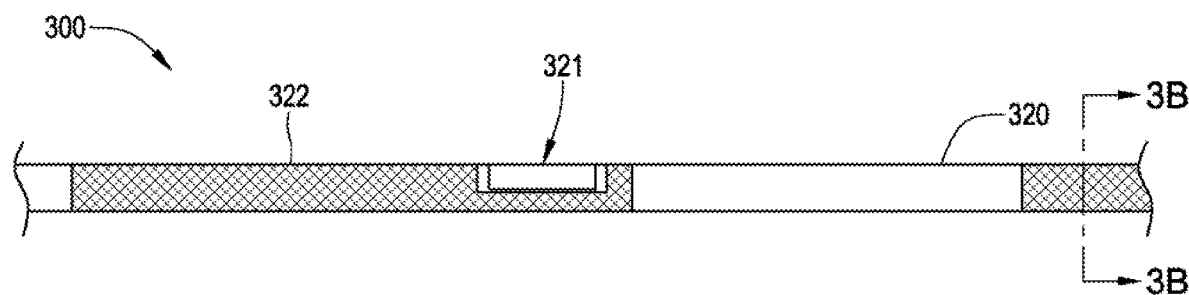
FIG. 3A is a side view of a partial intravascular catheter shaft assembly, in accordance with various embodiments of the present disclosure.

FIG. 3A is a partial front view of an intravascular catheter shaft 300 in accordance with various embodiments of the present disclosure. Importantly, aspects of the present embodiment decouple the torque and flexability/pushability attributes of braid 322 and shaft polymer 323. The catheter shaft 300 is shown without shaft polymer 323 in FIG. 3A to facilitate visualization of internal components. The braid 322 extends circumferentially around and along a length of a lumen bundle (as described in more detail in reference to FIG. 3B). In various embodiments the lumen bundle comprises a unibody core. In the present embodiment an MRI compatible catheter shaft is disclosed. One or more MRI compatible Balun coils 320 and a capacitor 321 of at least one of the Balun coils 320 may be coupled onto the braid 322. The MRI Balun coils 320 and the capacitor 321 may be electrically coupled to one another (e.g., via a soldered connection or electrical trace printed on to the braid). The capacitor 321 may be a printed capacitor which is directly printed onto the braid 322 (or onto a substrate applied to the braid 322). In some embodiments, the capacitor 321 is part of a Balun coil circuit (also commonly referenced to as an LC circuit or resonant circuit). In a magnetic or impedance-based catheter localization system, the capacitor 321 mitigates the Balun coils 320 from dispersing energy as heat.

Figure 3B:
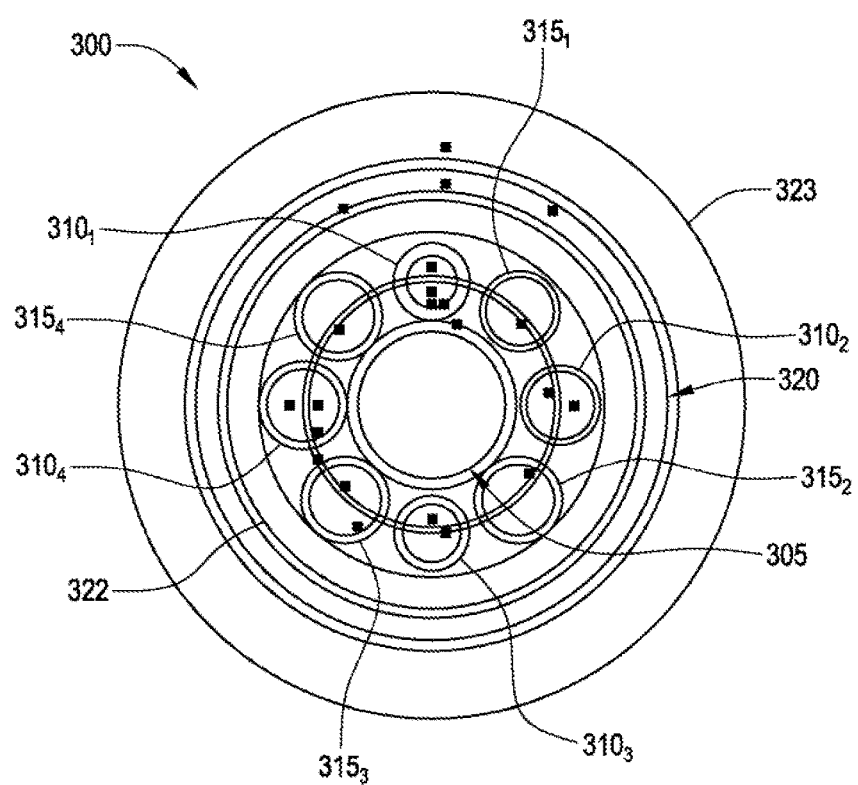
FIG. 3B is a cross-sectional view of the catheter shaft of FIG. 3A in accordance with various embodiments of the present disclosure.

As shown in FIG. 3A, at least one of the Balun coils 320 are coupled to a portion of the braid 322. In some specific embodiments, the Balun coils may be added via an additive building process (directly on to the braid). In yet other embodiments of the unibody cote, electrodes/traces may be printed directly to the core to facilitate various electrophysiology catheter functionality. As shown in FIG. 3B, a polyimide tubing extends around the unibody core and braid to seal the catheter shaft.

Embodiments of the present disclosure, in accordance with FIG. 3A, benefit from additional flexibility while achieving approximately 100% torque transmissivity across the length of the catheter shaft. In the PRIOR ART catheter shaft, these two attributes would be trade-offs. Moreover, catheter shafts in accordance with the present disclosure may achieve the desired characteristics while also facilitating reduced catheter diameter—by physically separating the structures of the catheter shaft which have the greatest impact on the various mechanical characteristics.

FIG. 3B is a cross-sectional view of the intravascular catheter shaft of FIG. 3A. The catheter shaft 300 includes a fluid lumen 305 extending through a longitudinal axis of the shaft, and electrical lumens $315_{1-4}$ and pull wire lumens $310_{1-4}$ circumferentially extending about the fluid lumen. The plurality of lumens form a lumen bundle, the lumen bundle being encompassed by a braid 322. The gaps between the lumens and the lumens and the braid may be filled with a polymeric material using a reflow process. The reflow process forming the unibody core. The unibody cores, in the present MRI compatible embodiment is further covered by an MRI Balun coil 320 and a polymer shaft 323. As the lumens, the braid 322, and the polymer shaft 323 all exist within unique physical spaces within the catheter shaft 300, the material characteristics of each may be selected to achieve independently tunable torque and pushability characteristics of the shaft. For example, one or more lumens may control the pushability characteristics of the shaft, and the braiding may be used to control the torquability characteristics.

One or more of the lumens, as shown in FIG. 3B, may be constructed from polyimide to permit adjustment of the pushability of the catheter shaft 300. While the present embodiment depicts a central fluid lumen 305 with eight smaller lumens circumferentially extending around the central lumen, various other lumen configurations are readily envisioned. Moreover, the purpose of each lumen may vary from those presented in the present embodiment, for example, one or more of the lumens may be for irrigation fluid, pull wires, electrical leads, etc. As shown in FIG. 3B, all or substantially all of the air gaps and spaces, outside of the lumens, may be filled with reflowed PEBAX®, for example. Such a design is more compact and benefits from independently adjustable mechanical characteristics.

While aspects of the unibody catheter shaft core of the present embodiment are illustrated with reference to LC circuits and MRI Balun coils, a skilled artisan will appreciate that such a unibody core may be implemented without such ancillary components.

Specific Experimental Embodiments

To illustrate the decoupling effect of the various unibody catheter shafts disclosed herein, several experimental catheter shafts were developed and tested. Each of the three experimental catheter shafts share the same unibody core (lumen structure and braid), with only the outer shaft polymer varying in thickness and/or durometer. In the three test shafts, an increase in wall thickness and/or durometer resulted in a (substantially) linear increase in shaft stiffness. Each of the test shafts underwent 3 point bending force testing, with the following results: approximately 0.25 pounds*force ("lbf"), approximately 0.63 lbf, and approximately 0.9 lbf. The experimental results evidence that the un-body catheter shaft construction disclosed herein facilitates the tuning of a catheter shaft, for various applications, by merely adjusting the durometer and/or wall thickness of the shaft polymer. As a result, a modular, unibody catheter shaft core may be developed and utilized across various product lines.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A deflectable catheter shaft comprising:
   a unibody core including
      a plurality of lumens extending parallel with a longitudinal axis of the catheter shaft,
      a braid circumferentially and longitudinally encompassing the plurality of lumens, and
      a reflowed polymeric material configured and arranged to fill gaps between the plurality of lumens and the braid; and
   wherein the catheter shaft is configured and arranged with independently tunable mechanical characteristics.

2. The catheter shaft of claim 1, wherein the plurality of lumens include a central fluid lumen extending co-axial with the longitudinal axis of the catheter shaft, and a plurality of electrical and pull-wire lumens circumferentially arranged about the central fluid lumen.

3. The catheter shaft of claim 1, wherein the catheter shaft is an introducer sheath, and the plurality of lumens include a central lumen configured and arranged to deliver an intravascular catheter to a distal end of the sheath, and a plurality of electrical, and/or pull-wire lumens extending around the central lumen.

4. The catheter shaft of claim 1, wherein the lumens are configured and arranged to transmit axial motion through the catheter shaft, and the braid is configured and arranged to transmit an axial torque through the catheter shaft.

5. The catheter shaft of claim 1, wherein the reflowed polymeric material and braid are distinct components from one another.

6. The catheter shaft of claim 1, further including a shaft polymer extending around the braid.

7. The catheter shaft of claim 1, further including a Balun coil and a capacitor coupled to an outer diameter of the braid, the Balun coil and capacitor are electrically coupled to one another.

8. The catheter shaft of claim 1, wherein the transmissivity of axial torque through the catheter shaft is 100%.

9. The catheter of claim 1, wherein the compression and torque characteristics of the catheter shaft are independent from one another.

10. An intravascular catheter comprising:
a proximal catheter shaft section including
a plurality of lumens extending along a longitudinal axis of the catheter shaft,
a proximal portion of a braid circumferentially and longitudinally encompassing the plurality of lumens, and
a reflowed polymeric material configured and arranged to fill gaps between the plurality of lumens and the braid; and
a distal catheter shaft section disposed at the distal end of the proximal catheter shaft section, the distal catheter shaft section including
a distal portion of the braid extending into the distal catheter shaft section, and
a Balun coil and a capacitor coupled to an outer diameter of the braid, and the Balun coil and the capacitor are electrically coupled to one another.

11. The catheter of claim 10, wherein proximal catheter shaft section is configured and arranged with independently tunable mechanical characteristics.

12. The catheter of claim 10, wherein the plurality of lumens include a central fluid lumen, and a plurality of electrical and pull-wire lumens extending around the central fluid lumen.

13. The catheter of claim 10, wherein the lumens are configured and arranged to transmit axial motion through the catheter shaft, and the braid is configured and arranged to transmit an axial torque through the catheter shaft.

14. The catheter of claim 10, wherein the reflowed polymeric material and braid are distinct components from one another.

15. The catheter of claim 10, further including a shaft polymer encompassing the braid along a length of the catheter shaft.

16. The catheter of claim 10, wherein the catheter shaft is magnetic resonance imaging compatible.

17. The catheter of claim 10, wherein the transmissivity of torque through the catheter shaft is 100%.

18. The catheter of claim 10, wherein the compression and torque characteristics of the catheter shaft are independent from one another.

19. The catheter of claim 7, further including a resonant circuit including the Balun coil and capacitor, wherein the capacitor of the resonance circuit is configured and arranged, in response to exposure to a magnetic or impedance-based catheter localization signal, mitigate the Balun coil from dispersing energy absorbed from the localization signal as heat.

20. The catheter shaft of claim 7 wherein the catheter shaft is magnetic resonance imaging compatible.

* * * * *